United States Patent [19]

Andrade et al.

[11] Patent Number: 4,608,443
[45] Date of Patent: Aug. 26, 1986

[54] METHOD FOR THE PREPARATION OF 1,4-BUTANDIAL

[75] Inventors: Juan Andrade, Kleinostheim; Günter Prescher, Hanau, both of Fed. Rep. of Germany; Marc Samson, Lokeren, Belgium

[73] Assignee: Degussa Aktiengesellschaft, Frankfurt, Fed. Rep. of Germany

[21] Appl. No.: 694,372

[22] Filed: Jan. 24, 1985

[30] Foreign Application Priority Data

Feb. 1, 1984 [DE] Fed. Rep. of Germany ....... 3403427

[51] Int. Cl.$^4$ .............................................. C07C 45/49
[52] U.S. Cl. .................................... 568/454; 568/465; 568/485; 568/494; 568/672
[58] Field of Search ............... 568/454, 496, 494, 497, 568/485, 465, 672

[56] References Cited

U.S. PATENT DOCUMENTS

| | | | |
|---|---|---|---|
| 2,288,211 | 6/1942 | Schuiz | 568/496 |
| 2,784,235 | 3/1957 | Smith et al. | 568/465 |
| 2,920,081 | 1/1960 | Privette et al. | 568/496 |
| 3,137,738 | 6/1964 | June | 568/596 |
| 4,161,616 | 7/1979 | Taylor et al. | 568/494 |
| 4,200,591 | 4/1980 | Hignett et al. | 568/454 |
| 4,306,086 | 12/1981 | Demay | 568/454 |
| 4,383,125 | 5/1983 | Harris et al. | 568/496 |
| 4,409,402 | 10/1983 | Himmele et al. | 568/496 |
| 4,414,420 | 11/1983 | Harris et al. | 568/496 |
| 4,418,216 | 11/1983 | Himmele et al. | 568/497 |
| 4,507,508 | 3/1985 | Hayden et al. | 568/494 |
| 4,533,756 | 8/1985 | Lin et al. | 568/454 |

FOREIGN PATENT DOCUMENTS

| | | | |
|---|---|---|---|
| 2537448 | 3/1977 | Fed. Rep. of Germany | 568/497 |
| 0878760 | 11/1981 | U.S.S.R. | 568/494 |

*Primary Examiner*—Werren B. Lone
*Attorney, Agent, or Firm*—Beveridge, DeGrandi & Weilacher

[57] ABSTRACT

The preparation of 1,4-butandial (succindialdehyde) is obtained using acrolein. The acrolein is first converted with an alkanol into 3,3-dialkoxy-1-propene and this is then hydroformylated in the presence of hydridotristriphenylphosphine-rhodiumcarbonyl mixed with triphenylphosphine or triphenylphosphite as the catalyst. The thereby obtained 4,4-dialkoxy-butanal is removed from the hydroformylation product by means of distillation and is then hydrolyzed to 1,4-butandial.

6 Claims, No Drawings

METHOD FOR THE PREPARATION OF 1,4-BUTANDIAL

The invention pertains to the method for the preparation of 1,4-butandial (succindialdehyde) from acrolein by the conversion of the acrolein in an acetal, hydroformylation of the acetal and hydrolysis of the hydroformylation product.

It is known to prepare 1,4-butandial by chlorinating tetrahydrofuran and then hydrolyzing the resulting 2,5-dichlorotetrahydrofuran or the thereby produced 2,5-dialkoxytetra-hydrofuran to 1,4-butandial (DD-PS No. 25656). A disadvantage resides in the fact that with this process, the yield is poor particularly with the chlorination.

It also known to obtain 1,4-butandial from acrolein. In this method, the acrolein is first formed into allylidendiacylate, the latter is then hydroformylated to 4,4-diacyloxybutyraldehyde, which in turn is thereafter through conversion with an alkanol formed into 2,5-dialkoxytetrahydrofuran and finally this is hydrolyzed into 1,4-butandial (U.S. Pat. No. 2,920,081). This process, too, provides only mediocre yields and is in addition complicated and accordingly not desirable for utilization on a commercial scale.

It is still further known to initially produce acetal from acrolein and then to hydroformylate the acetal in the presence of a cobalt catalyst at a temperature of 120° to 200° C. under a pressure of 50 to 300 bar and then to hydrolyze the hydroformylation product (British Pat. No. 702,206). According to this process, the acetals of the acroleins are produced in poor yields with lower weight alkanols, that is acyclic acetals, while the hydroformylation reaction proceeds with acetals of the acroleins with polyfunctional alkanols, that is with cyclic acetals, considerably better, but the yields of 1,4-butandial is nevertheless unsatisfactory.

It has now been found according to the present invention that 1,4-butandial can be prepared by a method utilizing acrolein by conversion of the acrolein into an acetal, hydroformylating the acetal and hydrolyzying the hydroformylation product, wherein the process is carried out by the steps comprising:

(a) converting the acrolein into 3,3-dialkoxy-1-propene;

(b) then hydroformylating in the presence of hydrido-tris-triphenylphosphine-rhodiumcarbonyl as well as triphenylphosphine and preferably, or triphenylphosphite as catalysts;

(c) separating by distillation the 4,4-dialkoxybutanal from the hydroformylation product; and (d) hydrolyzing this to 1,4-butandial.

This method provides considerably improved yields of 1,4-butandial compared to the known methods. In this respect, in particular, the step of hydroformylation is determinative. This is because heretofore, the hydroformylation of acyclic acetals was not useable in a practicable manner and as a result thereof the preparation of 1,4-butandial in this respect was not a feasible reality, so for that reason the inventive hydroformylation of these acetals is carried out with such outstanding results that the formation of 1,4-butandial by these ways is particularly advantageous.

For the carrying out of the method of the present invention, the acrolein is converted with an alkanol into a 3,3-dialkoxy-1-propene. Preferably, a 3,3-dialkoxy-1-propene is chosen so that in each alkoxy group, there is 1 to 6 carbon atoms. In particular, the 3,3-dimethoxy-1-propene and the 3,3-diethyl-1-propene are preferred. The conversion is carried out by known methods, such as for example, as shown in the Org. Synth. Coll., Vol. 4, (1963), pp. 21–22 (relied on and incorporated herein by reference) which describes the method for preparation using the selected alkanols with the acrolein in the presence of strong acid as catalysts.

Advantageously for the preparation of the 3,3-dimethoxy-1-propene and the 3,3-diethoxy-1-propene, the method described in the concurrently filed patent application German P No. 34 03 426.9 (corresponding to U.S. application Ser. No. 694,371) can be used. According to this method, the acrolein is converted with alkanol in the presence of a solid acidic catalyst, such as strongly acidic ion exchanger or strongly acidic zeolites, and the 3,3-dialkoxy-1-propene is obtained and, after the removal of the catalyst material, the reaction mixture is extracted with water insoluble organic solvents and the extract is fractionally distilled.

For the further carrying out of the method of the invention, the 3,3-dialkoxy-1-propene is hydroformylated by means of conversion with a gas mixture of hydrogen and carbon monoxide in the presence of a catalyst. This conversion is carried out in an efficient manner at elevated temperatures, especially at a temperature between about 100° and 140° C. The pressure can be widely varied as desired; however, it is in general desirable to carry out the process at least at normal pressure. Preferably, the pressure is between about 1 and 6 bar. It is desirable to use at least stoichiometric quantities, preferably excess amounts, of hydrogen and carbon monoxide whereby the molecular ratio of the hydrogen to carbon monoxide can be widely varied as desired, preferably however, between 0.5 to 1 to 1 to 0.5.

With the hydroformylation, the catalyst which serves for this purpose is hydridotris-triphenylphosphinerhodiumcarbonyl in a mixture with triphenylphosphine, or preferably triphenylphosphite. These catalysts are described in DE-AS No. 1,793,069 and are known in the art. Advantageously for the carrying out of the process of the invention, the weight ratio based on one part by weight of 3,3-dialkoxy-1-propene ranges from about 0.0001 to 0.0025 parts by weight of hydridotriphenylphosphine-rhodiumcarbonyls and 0.04 to 0.06 parts by weight of the triphenylphosphine or triphenylphosphite.

The hydroformylation product is fractionally distilled in order to obtain the 4,4-dialkoxybutanal. With this, there is advantageously utilized a reduced pressure, preferably with the pressure below 50 mbar.

The 4,4-dialkoxybutanal obtained thereby is subsequently converted into the 1,4-butandial through hydrolysis. The hydrolysis is carried out in an acidic medium, preferably in a strongly acidic medium, with a particular advantage in carrying out the process in the presence of an acidic ion exchanger, advantageously at a temperature below 30° C., preferably at a temperature between 5° and 15° C. Many suitable acidic ion exchangers, e.g. resins, may be used for purposes of the invention.

The following examples serve to illustrate the invention without limiting it in any respect.

EXAMPLE 1

Into a mixture of 146 g (2.6 mol) acrolein and 480 g (3.2 mol) orthoformic acid ethyl ester, a warm solution of 12 g of ammonium nitrate in 170 ml anhydrous ethanol is introduced. The mixture is permitted to stand for 6 hours, then filtered and converted with 13 g sodium carbonate and fractionally distilled. The fraction which is obtained in the temperature range of 120° to 125° C. contained the resulting 3,3-diethoxy-1-propene. The yield amounted to 260 g (2.0 mol) which corresponding to 77%, based on the introduced acrolein. The 3,3-diethoxy-1-propene, in a stirred autoclave, is contacted with 9.4 g triphenylphosphite and 0.4 g hydridotrie-triphenylphosphinerhodiumcarbonyl. This was formed into a mixture under 3 bar pressure charged with an equal volume of hydrogen and carbon monoxide. The temperature in the autoclave was held at 110° C. After 140 minutes, no further gas was taken up and the charging was ended. By means of gas chromatography, it was determined that 99.5% of the 3,3-diethoxy-1-propene was converted. The conversion mixture included 4,4-diethoxy-butanal and 2-methyl-3,3-diethoxy-propanal in a mol ratio of 8.5 to 1. The conversion mixture is then distilled at 20 mbar. The desired 4,4-diethoxybutanal was obtained at 90° to 91° C. It was dissolved in an equal volume of water and the solution was converted with 60 g ion exchange resin Dowex MSC-1. The mixture was stirred for 2 hours at 20° and then filtered. The filtrate was a 25% aqueous solution of the 1,4-butandial. The yield of the 1,4-butandial, based on the introduced 3,3-diethoxy-1-propene, amounted to 80%.

EXAMPLE 2

The process was carried out according to Example 1, however 208 g (1.6 mol) of the 3,3-diethoxy-1-propene was mixed with 7.5 g triphenylphosphine and 0.4 g of hydridotristriphenylphosphine-rhodiumcarbonyl, and the hydroformylation was carried out at 5 bar. 99.5% of the 3,3-diethoxy-1-propene was converted. The conversion mixture contained 4,4-diethoxy-butanal and 2-methyl-3,3-diethoxy-propanal in a mol ratio of 5.1 to 1. The yield of 1,4-butandial, based on the introduced 3,3-diethoxy-1-propene amounted to 71%.

EXAMPLE 3

The process was carried out according to Example 1, however 196 g (1.5 mol) of the 3,3-diethoxy-1-propene was contacted with 9.4 g triphenylphosphite and 0.4 g hydridotristriphenylphosphate-rhodiumcarbonyl. The conversion was carried out at 140° C.; the uptake of gas after 200 minutes was concluded. 99.4% of the 3,3-diethoxy-1-propene was converted. The conversion mixture contained the 4,4-diethoxy-butanal and 2-methyl-3,3-diethoxy-propanal in a mol ratio of 11.2 to 1. The yield of 1,4-butandial, based on the introduced 3,3-diethoxy-1-propene amounted to 86%.

EXAMPLE 4

On an hourly basis, 169.3 g (3.02 mol) acrolein was mixed with 189.1 g (5.91 mol) methanol in a concurrent stream in a loop reactor. To this stream, there was continuously added unreacted initial acrolein and methanol which was recovered from the conversion mixture. In the circulation system of the reactor, the mixture was streamed through a zone filled with 100 g of strongly acidic ion exchange resin (Dowex MSC-1). The temperature in the reaction was held at 17° C. and the average dwell time was 2.3 hours. The conversion mixture was then withdrawn from the reactor in a concurrent stream and was then lead to the middle of a pulsating extraction column. Into this column on an hourly basis, there was introduced from the top 1810 g water and at the bottom, 810 g n-octane. The temperature in the column was 20° C. The phases withdrawn from the top and bottom were then fractionally distilled. With this, there was obtained on an hourly basis from the upper phase 290 g (2.84 mol) 3,3-dimethoxy-1-propene. In addition, there was obtained on an hourly basis from the upper phase 6.0 g acrolein and from the bottom phase, 111.1 g acrolein and 450.9 g methanol was recovered. There was accordingly 59.1% overall hourly conversion of the introduced 286.4 g acrolein. The recovered acrolein and methanol were continuously recycled to the loop reactor. The 3,3-dimethoxy-1-propene was 98%. The boiling point was 89° to 90° C. The yield, based on the converted acrolein, amounted to 94%. Overall, the process was carried out according to Example 1, however 204.3 g (2.0 mol) of the obtained 3,3-dimethoxy-1-propene was introduced into the stirred autoclave. 99.5% of the 3,3-dimthoxy-1-propene was converted. The conversion mixture contained 4,4-dimethoxy-butanal and 2-methyl-3,3-dimethoxypropanal in a mol ratio of 10.3 to 1. The conversion mixture was distilled at 18 mbar. The desired 4,4-dimethoxy-butanal was obtained at 69° to 70° C. It was then treated in accordance with the procedures in Example 1. The yield of 1,4-butandial, based on the introduced 3,3-dimethoxy-1-propene, amounted to 79%.

Further variations and modifications of the invention will become apparent to those skilled in the art from the foregoing and are intended to be encompassed by the claims appended hereto.

The entire disclosure of the German priority application No. P 34 03 427.7 is relied on and incorporated herein by reference.

Applicants rely on and incorporate by reference the related application Ser. No. 694,371 filed concurrently herewith corresponding to German No. P 34 03 426.9.

We claim:

1. Method for the preparation of 1,4-butandial comprising reacting acrolein with an alkanol to form 3,3-dialkoxy-1-propene as a product, wherein the alkoxy group has from 1 to 6 carbon atoms, contacting the said 3,3- dialkoxy-1-propene with a mixture of hydrogen and carbon monoxide as the synthesis gas and hydridotris-triphenylphosphine-rhodiumcarbonyl, and triphenylphosphine or triphenylphosphite thereby to carry out a hydroformylating reaction to obtain a hydroformylation product containing 4,4-dialkoxybutanal distilling said hydroformylation product to thereby separate the 4,4-dialkoxybutanal therefrom and hydrolyzing said butanal to 1,4-butandial.

2. The method according to claim 1, further comprising utilizing 0.0001 to 0.0025 parts by weight of the hydridotristriphenylphosphine-rhodiumcarbonyl per part by weight of 3,3-dialkoxy-1-propene.

3. The method according to claim 1, further comprising utilizing 0.04 to 0.06 parts by weight of triphenylphosphine or triphenylphosphite per part by weight of 3,3-trialkoxy-1propane.

4. The method according to claim 1, further comprising carrying out the hydroformylation reaction at a temperature of 100° to 140° C. under pressure of 1 to 6 bar.

5. The method according to claim 1, further comprising wherein the alkanol is methanol.

6. The method according to claim 1, further comprising wherein the alkanol is ethanol.

* * * * *